United States Patent [19]

Struble et al.

[11] Patent Number: 5,419,684
[45] Date of Patent: May 30, 1995

[54] INFUSION PUMP WITH REVERSIBLE MOTOR AND METHOD OF USE

[75] Inventors: Kent R. Struble, Mahtomedi; Steven H. Stolle, Columbia Heights; Rodney J. Smith, Hastings; Michael R. Plumb, Shoreview; Paul G. Izen, Woodbury, all of Minn.

[73] Assignee: Minnesota Mining and Manufacturing Company, St. Paul, Minn.

[21] Appl. No.: 76,813

[22] Filed: Jun. 14, 1993

[51] Int. Cl.6 ............................................. F04B 43/08
[52] U.S. Cl. .................................. 417/44.2; 417/474; 417/326; 417/53
[58] Field of Search .............. 417/44 A, 44 R, 53, 417/43, 474, 477 R, 477 A, 478, 479, 326

[56] References Cited

U.S. PATENT DOCUMENTS

| | | | |
|---|---|---|---|
| 3,827,828 | 8/1974 | Edwards | 417/43 |
| 3,951,570 | 4/1976 | De Biaggi | 417/475 |
| 4,236,880 | 12/1980 | Archibald | 417/478 |
| 4,277,226 | 7/1981 | Archibald | 417/38 |
| 4,322,201 | 3/1982 | Archibald | 417/279 |
| 4,382,753 | 5/1983 | Archibald | 417/479 |
| 4,391,600 | 7/1983 | Archibald | 604/153 |
| 4,410,322 | 10/1983 | Archibald | 604/153 |
| 4,431,425 | 2/1984 | Thompson et al. | 604/246 |
| 4,601,702 | 7/1986 | Hudson | 604/246 |
| 4,602,249 | 7/1986 | Abbott | 340/605 |
| 4,657,490 | 4/1987 | Abbott | 417/478 |
| 4,660,607 | 4/1987 | Griffith et al. | 141/1 |
| 4,661,045 | 4/1987 | Winston et al. | 417/477 R |
| 4,755,168 | 7/1988 | Romanelli | 417/476 |
| 4,836,752 | 6/1989 | Burkett | 417/474 |
| 4,840,542 | 6/1989 | Abbott | 417/9 |
| 5,017,192 | 5/1991 | Dodge et al. | 604/250 |
| 5,055,001 | 10/1991 | Natwick et al. | 417/63 |
| 5,078,362 | 1/1992 | Lawless et al. | 251/9 |
| 5,096,385 | 3/1992 | Georgi et al. | 417/474 |
| 5,103,214 | 4/1992 | Curran et al. | 340/691 |
| 5,116,203 | 5/1992 | Natwick et al. | 417/53 |
| 5,158,437 | 10/1992 | Natwick et al. | 417/53 |
| 5,180,287 | 1/1993 | Natwick et al. | 417/43 |
| 5,211,548 | 5/1993 | Okada | 417/474 |
| 5,217,355 | 6/1993 | Hyman | 417/474 |
| 5,302,093 | 4/1994 | Owens et al. | 417/479 |

FOREIGN PATENT DOCUMENTS

WO91/19523 12/1991 WIPO ................ A61M 5/142

OTHER PUBLICATIONS

"AVI Guardian ® 100 and Micro 110 Volumetric Infusion Pump Service Manual"; AVI Part No. 936023 D; 1984.

Folder entitled "AVI Infusion Therapy Systems 'When it all depends on you, depend on us' 3M Health Care" which includes the following brochures: AVI 200A Infusion Pump; AVI Micro 210A Infusion Pump; AVI 400A Infusion Pump; AVI 840 Dual Channel Infusion Pump; AVI Micro 845 Dual Channel Infusion Pump; AVI 285 and 285CM Micro Infusion Pump; AVI 480 and 480CM Infusion Pump; AVI 600 Syringe Pump; AVI Administration Sets—Infusion Pump Sets; Medifuse ® Setting the Standard for Homecare Patient IV Delivery Systems; AVI Nurse Clinician Services; 3M IV Poles—3M delivers space-saving solutions; and The 3M IV Flow Regulator.

*Primary Examiner*—Richard A. Bertsch
*Assistant Examiner*—Peter Korytnyk
*Attorney, Agent, or Firm*—Gary L. Griswold; Walter N. Kirn; Stephen W. Bauer

[57] ABSTRACT

An infusion pump for regulating fluid flow through the flow path of an IV tubing set for intravenous administration to a patient. The pumping mechanism of the infusion pump comprises a reversible motor having a drive shaft with a wheel mounted thereon. A valve is provided which is adapted for reversibly closing the flow path through the IV tubing set, and a swing arm is provided. The swing arm has a wheel-engaging portion adapted for engaging the wheel, and an actuator portion operatively linked with the valve to actuate the valve. The arrangement is such that, when the motor is turning the drive shaft in a first direction, the swing arm is moved towards a first position where the actuator portion allows the valve to move to its open position to open the flow path. When the motor is reversed to turn the drive shaft in a second direction opposite the first direction, the swing arm is moved to a second position where the actuator portion moves the valve to its closed position to close the flow path. An infusion therapy system and a method of use of the infusion pump are also disclosed.

34 Claims, 8 Drawing Sheets

INFUSION PUMP WITH REVERSIBLE MOTOR AND METHOD OF USE

This invention relates generally to infusion pumps for regulating the flow of fluids, and more particularly to an infusion pump which is adapted to relieve fluid pressure in the IV line downstream of the pump when the pump is turned off.

BACKGROUND OF THE INVENTION

Pumps used in infusion therapy typically have pressure sensing mechanisms and respond in some fashion to pressure levels indicative of a fault condition. For example, a sudden rise in the pressure of the fluid in the IV delivery tubing may be indicative of some occlusion in the line between the pump and the patient. In such a case, the infusion pump stops pumping fluid and provides an audible and visual alarm to alert a human operator to the presence of the fault.

It is also desirable for the pump to react in two further ways. First, the pump should close the fluid pathway until the human operator takes positive steps to set the condition right. The rationale for this reaction is that, if the occlusion should clear spontaneously, there would be an open flow path, possibly allowing gravity flow in excess of the planned regimen. Second, the pump should relieve pressure in the IV line between the pump and the occlusion to prevent delivering a sudden bolus of pressurized fluid to the patient when the occlusion is cleared.

These two reactions are accomplished in the infusion pump sold under the trade designation "Model 480", for example, by Minnesota Mining and Manufacturing Company, St. Paul, Minn. This infusion pump is used with a tubing assembly having a cassette with two pumping chambers generally as disclosed in coassigned U.S. Pat. Nos. 4,236,880; 4,277,226; 4,322,201; 4,382,753; 4,391,600; and 4,410,322, which are hereby incorporated by reference. When an occlusion fault condition is detected, the motor is reversed so as to relieve pressure between the pump and the occlusion site.

Figure 1:
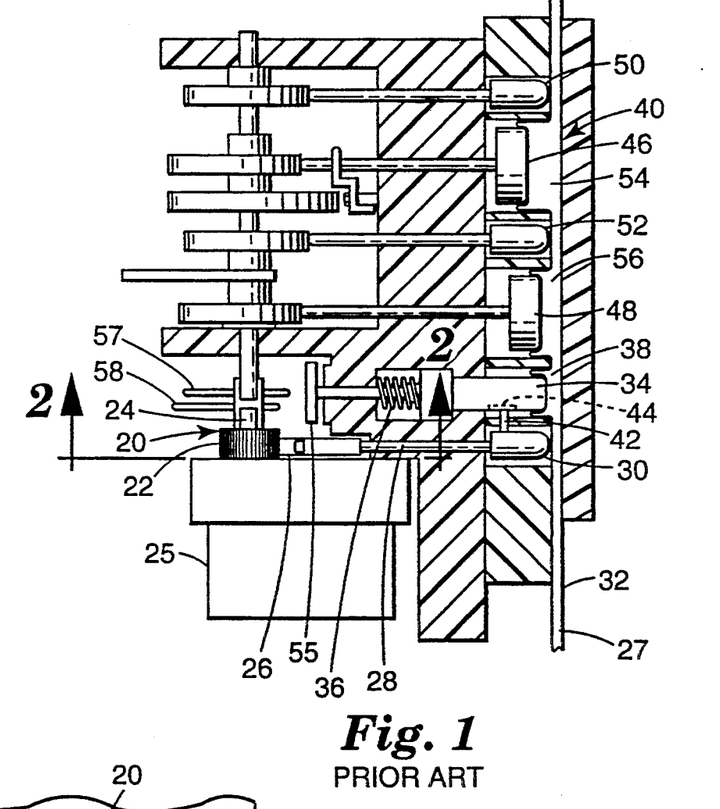
FIG. 1 is a cross-sectional view through the pumping mechanism of a prior infusion pump manufactured by Minnesota Mining and Manufacturing Company, St. Paul, Minn.
Figure 2:
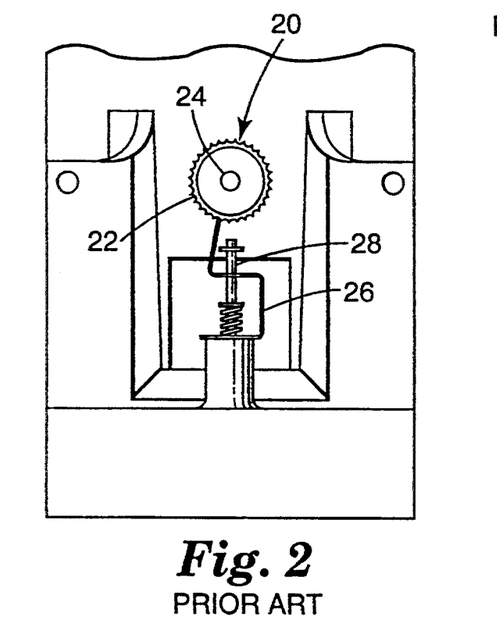
FIG. 2 is an enlarged view along line 2—2 of FIG. 1 illustrating details of the prior infusion pump.

FIGS. 1 and 2 illustrate various details of the "Model 480" infusion pump. The "Model 480" infusion pump has a mechanism for closing the IV tubing to fluid flow as the pump motor 25 is reversed. That mechanism includes a wheel 20, having a ratcheted or knurled circumference 22, mounted on the drive shaft 24 of the motor 25. A generally Z-shaped spring 26 is mounted in the infusion pump, with one end of the "Z-spring" 26 continually sliding past the ratcheted circumference 22 of the wheel 20 when the drive shaft 24 is rotating in the normal, forward direction (clockwise in FIG. 2). When the drive shaft 24 is rotating in the normal, forward direction, the infusion pump is pumping IV fluid in the downstream direction to regulate the flow of the fluid.

When the pump motor 25 reverses the direction of rotation of the wheel 20 (now counterclockwise in FIG. 2) to relieve pressure in the IV tubing 27 downstream of the infusion pump, the Z-spring 26 catches the ratcheted circumference 22 of the wheel 20. And, when the Z-spring 26 catches the circumference 22, the Z-spring 26 bends and applies pressure to a valve stem 28 to close a ribbed "overpressure" valve 30, thereby occluding the lumen of the IV tubing set 32. In practice, the Z-spring 26 allows the drive shaft 24 to back up about one eighth of a turn before closing the valve 30.

The valve 30 in the "Model 480" infusion pump serves an additional purpose of occluding flow through the lumen of the IV tubing until pressure upstream of the valve 30 builds up to a predetermined amount. See, in particular, coassigned U.S. Pat. No. 4,322,201. An overpressure piston 34 is provided with a spring-biasing mechanism 36 to hold the overpressure valve 30 in its closed position until a predetermined cracking pressure is exerted by an overpressure chamber 38 of the pumping cassette 40 against the overpressure piston 34. During normal operation of the infusion pump, once this predetermined cracking pressure is obtained, the overpressure piston 34 allows a pin 42 mounted on the overpressure valve 30 to move along a longitudinally-extending slot 44 in the piston 34 to permit the overpressure valve 30 to open or close.

The overpressure piston 34 also includes a mechanism to trigger an alarm or signal in response to high fluid pressure in the overpressure chamber 38. That mechanism comprises a circular contact plate 55 mounted on the piston, which will engage one or both of two telescoping, spring-loaded, overpressure contact probes 57 or 58. Contact probes 57 and 58 are positioned and adapted to provide an alarm signal indicating high fluid pressure in the overpressure chamber 38, which may indicate that the IV line downstream of the infusion pump is occluded. A microprocessor (not shown) receives the signal indicating an overpressure condition, and reverses the motor 25 until the overpressure condition is relieved, at which point the infusion pump stops and enters the standby mode.

First and second pumping pistons 46 and 48 and first and second valves 50 and 52 are also provided in the "Model 480" infusion pump, and are also described in U.S. Pat. No. 4,322,201. The pistons 46 and 48 act on pumping chambers 54 and 56 to pump fluid through the cassette 40.

While the Z-spring mechanism has been successful in use, it has been difficult to manufacture and assemble in the infusion pump. In order to obtain consistent results with the spring, much time and care must be taken by skilled production workers.

SUMMARY OF THE INVENTION

This invention provides an infusion pump and an infusion therapy system for regulating fluid flow through the flow path of an IV tubing set for intravenous administration to a patient. The infusion pump and infusion therapy system have a mechanism for relieving pressure in the IV line downstream of the infusion pump as operation of the infusion pump is stopped, e.g., because the infusion pump is turned off or in response to an alarm signal. The mechanism closes the IV line to prevent additional fluid flow until after the infusion pump is restarted. The invention also provides such a mechanism that can be economically manufactured and assembled, and which provides consistent results.

Generally, the infusion pump of the invention comprises a pumping mechanism adapted for regulating fluid flow through the IV tubing set. The pumping mechanism comprises a reversible motor having a drive shaft with a wheel mounted thereon. A valve is provided which is adapted for reversibly closing the flow path through the IV tubing set. The valve has an open position, wherein the valve is adapted not to close the flow path through the IV tubing set, and a closed position, wherein the valve is adapted to close the flow path through the IV tubing set. A swing arm is also provided having a wheel-engaging portion adapted for engaging the wheel and an actuator portion operatively linked with the valve. The arrangement is such that, when the motor is turning the drive shaft in a first direction, the swing arm is moved towards a first position where the actuator portion moves the valve to its open position or allows the valve to move to its open position to open the flow path. When the motor is reversed to turn the drive shaft in a second direction opposite the first direction, the swing arm is moved to a second position where the actuator portion moves the valve to its closed position or allows the valve to move to its closed position to close the flow path.

Preferably, an occlusion detection means is provided for detecting an occlusion in the flow path and providing a signal representing the occlusion. The motor is reversed in response to a signal representing an occlusion fault being received from the occlusion detection means, and the swing arm is moved from its first position to its second position when the motor is reversed. Most preferably, the occlusion detection means comprises a solid state electronic pressure sensor mounted in the infusion pump for sensing fluid pressure in the IV tubing.

Also, preferably, the swing arm is pivotably mounted on a pivot point, with the wheel-engaging portion of the swing arm engaging the wheel only within a limited range of rotation about the pivot point to move the swing arm between its first and second positions. An urging means, such as a torsion spring, is provided to urge the swing arm toward the wheel when the swing arm is in either of its first or second positions such that the wheel engages the wheel-engaging portion of the swing arm when the motor is reversed to move the swing arm to the other of its first or second positions.

The wheel and wheel-engaging portion of the swing arm preferably include intermeshing teeth. Preferably, the swing arm also has a second wheel-engaging portion comprising a generally concave, toothless, ramping surface. The teeth of the wheel run along the ramping surface, without engaging the teeth of the wheel-engaging portion of the swing arm, when the swing arm is in its first position and the motor is turning in its first direction. The arrangement is such that, when the direction of the motor is changed to its second direction, the ramping surface of the swing arm is moved by the wheel to bring the teeth of the first wheel-engaging portion of the swing arm into intermeshing relationship with the teeth of the wheel.

Most preferably, the actuating portion of the swing arm engages the valve to close the flow path when the actuating portion is in its second position, and the wheel comprises two arm-engaging portions. The wheel of this preferred embodiment includes a first arm-engaging portion having the aforesaid teeth for intermeshing engagement with the teeth of the swing arm, and a second arm-engaging portion offset axially along the wheel from the first arm-engaging-portion. The swing arm of this preferred embodiment includes a third wheel-engaging portion for engaging the second arm-engaging portion of the wheel when the swing arm is in its second position. The arrangement is such that the second arm-engaging portion of the wheel holds the swing arm in its second position when the motor is turning in its second direction, thereby holding the valve in its closed position without the teeth of the first-wheel engaging portion of the swing arm engaging the teeth of the first arm-engaging portion of the wheel.

When the direction of the motor is changed from its second direction to its first direction, the second arm-engaging portion of the wheel moves the third wheel-engaging portion of the swing arm to pivot the swing arm and bring the teeth of the first wheel-engaging portion of the swing arm into intermeshing relationship with the teeth of the first arm-engaging portion of the wheel.

Most preferably, the third wheel-engaging portion of the swing arm comprises a roller that is in rolling engagement with the second arm-engaging portion of the wheel when the swing arm is in its second position but that is disengaged from the wheel as the swing arm is moved toward its first position.

Also, preferably, an axle is mounted in the pump for pivotably mounting the swing arm, and the swing arm is elongate and has an elongate bore for receiving the axle. As used herein, "elongate bore" refers to a bore having an elongate cross section. The elongate bore permits longitudinal movement of the swing arm within a limited range of longitudinal movement. A suitable biasing means, such as a compression coil spring, is also provided for biasing the swing arm in the longitudinal direction relative to the axle generally toward the wheel.

The actuating portion of the swing arm preferably allows the valve to move to its open position when the swing arm is in its first position, and actuates the valve to close the valve when the swing arm is in its second position.

Preferably, the valve comprises a valve member movable between the open and closed positions, a stem extending from the valve member, and a spring-loaded mechanism mounted on the stem for engagement with the actuating portion of the swing arm to move the valve member to its closed position when the swing arm moves to its second position while providing a short delay before shutting off the flow of fluid through the IV tubing with the valve. For example, the spring-loaded mechanism may include an actuating member mounted on the stem for axial movement along the stem, a spring mounted on the stem for biasing the actuating member in the direction toward the actuating portion of the swing arm, and a stop on the stem for limiting axial movement of the actuating member such that the actuating member does not engage the actuating portion of the swing arm until the swing arm is moved toward its second position.

The valve member is preferably free to move within a range of axial motion when the swing arm is in its second position such that the valve member is adapted to be biased toward its open position by the IV tubing set.

Most preferably, the infusion therapy system includes an IV tubing set having a pumping cassette. The pumping cassette has one or more pumping chambers for pumping fluid through the IV tubing and an overpressure chamber responsive to pressure in the IV tubing. The infusion pump further comprises an overpressure piston responsive to pressure in the overpressure chamber and operatively linked with the valve member such that the valve member is held in its closed position by the overpressure piston until a predetermined cracking pressure is exerted by the overpressure chamber against the overpressure piston, For example, the overpressure piston may comprise a spring-loaded piston having biasing means adapted for biasing the piston against the overpressure chamber of the IV tubing set. The overpressure piston of this example includes a releasable valve-holding means for holding the valve member in its closed position until a predetermined cracking pressure is exerted by the overpressure chamber against the overpressure piston. The valve-holding means does not prevent movement of the valve member between its open and closed positions once the predetermined cracking pressure has been exceeded. The valve member includes a pin extending from the valve member, and the releasable valve-holding means comprises a pin-receiving slot extending generally in the longitudinal direction along the piston. The pin-receiving slot has an end adapted to engage the pin to hold the valve member in its closed position until the piston is displaced as the overpressure chamber exceeds the predetermined cracking pressure.

Most preferably, a door is mounted on the infusion pump, and a floating pressure plate is mounted in the door of the infusion pump. The floating pressure plate holds the IV tubing set in operative position relative to the pumping mechanism when the door is closed. The pressure plate is biased toward the pumping mechanism and the valve to hold the IV tubing set between the pressure plate and the pumping mechanism. When in its closed position, the valve presses the IV tubing set against the pressure plate to close the fluid path.

Alternatively, the teeth of the swing arm include one elastomeric tooth adjacent the opposite side of the swing arm from the second wheel-engaging portion of the swing arm.

Generally, the method of the invention employs the infusion pump to close the fluid path through the IV tubing in response to a fault condition, such as an occlusion in IV tubing, in a manner designed to avoid supplying a bolus of IV fluid to the patient when the fluid path is closed. The method generally comprises pumping IV fluid in the downstream direction toward the patient through IV tubing with the pumping mechanism, and reversing the direction of the pump-driving motor when turning off the pump or detecting a fault condition such that the direction of rotation of the wheel is reversed and fluid is pumped in the upstream direction away from the patient. When the rotation of the wheel is reversed, the swing arm is pivoted from a first position, in which the valve is allowed to be in an open position allowing fluid flow through the IV tubing, to a second position, in which the valve is moved to a closed position closing the IV tubing to fluid flow. In response to the swing arm being pivoted from its first position to its second position, the valve is moved to its closed position from its open position by actuating the valve with the swing arm.

When the pumping mechanism of the infusion pump is turned on, the valve is allowed to open as the swing arm is moved from its second position to its first position by the wheel, thereby allowing pump-regulated fluid flow through the IV tubing.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 3:
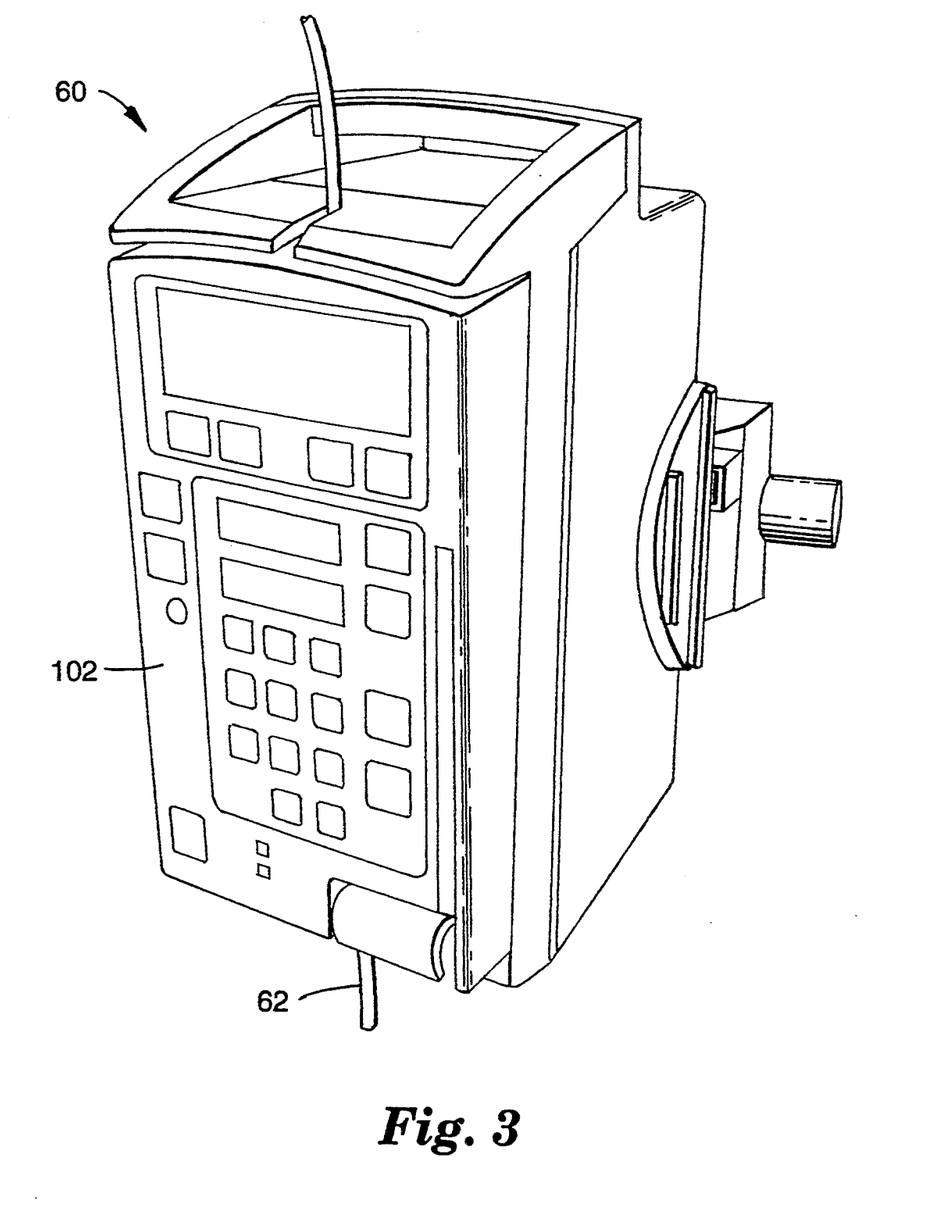
FIG. 3 is a perspective view of an infusion pump of the invention.

The infusion pump is designated in its entirety by the reference numeral 60 in FIG. 3, and may be of the general type described in coassigned U.S. Pat. Nos. 4,236,880; 4,277,226; 4,322,201; 4,382,753; 4,391,600; 4,410,322; 5,017,192; and 5,103,214; and coassigned U.S. patent application Ser. Nos. 07/797,691 (filed Nov. 25, 1991); 07/917,593 (filed Jul. 23, 1992); and 07/976,404 (filed Nov. 13, 1992), all of which are hereby incorporated by reference. The infusion pump 60 is adapted to regulate fluid flow through the flow path of an IV tubing set 62 for intravenous administration to a patient.

Figure 4:
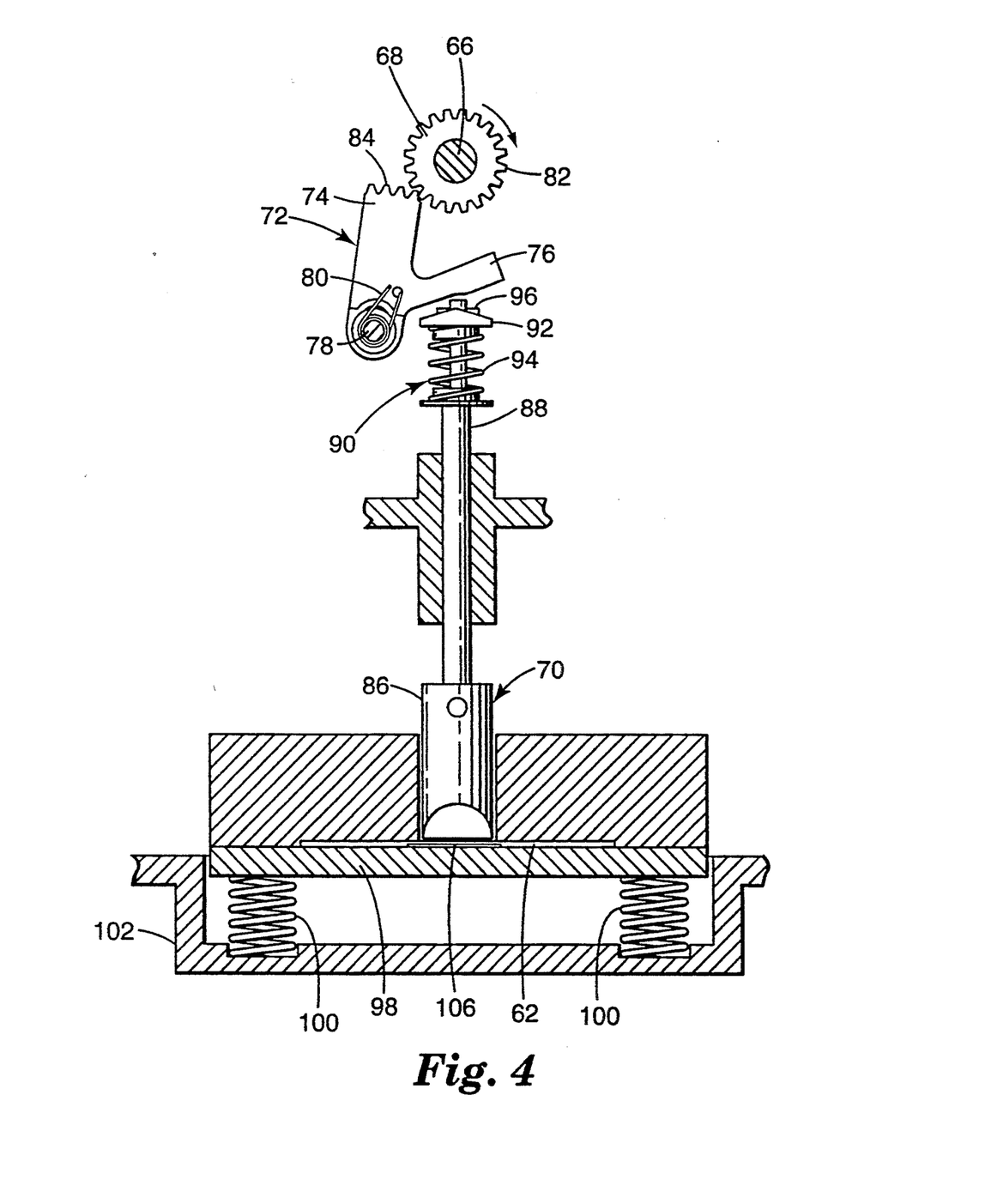
FIG. 4 is a cross sectional view similar in some respects to FIG. 2 illustrating a novel swing arm/valve arrangement in their normal operating positions allowing flow through an IV tubing set placed in the infusion pump.

The infusion pump 60 generally comprises a conventional pumping mechanism (similar to first and second pistons 46 and 48 shown in FIG. 1) adapted for regulating fluid flow through the IV tubing set 62. As illustrated in FIG. 4, the pumping mechanism includes a reversible motor 64 (seen in side view in FIG. 5) having a drive shaft 66 with a wheel 68 mounted thereon. The drive shaft 66 also provides a linkage to the pumping pistons, which in preferred embodiments of the infusion pump 60 are similar to those described above as first and second pistons 46 and 48.

The infusion pump 60 also includes a valve 70 adapted for reversibly closing the flow path through the IV tubing set 62. The valve 70 has an open position (FIG. 4), wherein the valve 70 is adapted not to close the flow path through the IV tubing set 62. The valve 70 also has a closed position (FIG. 6), wherein the valve 70 is adapted to close the flow path through the IV tubing set 62. A swing arm 72 is provided having a wheel-engaging portion 74 adapted for engaging the wheel 68 and an actuator portion 76 operatively linked with the valve 70.

The arrangement is such that, when the motor 64 is turning in a first direction (clockwise in FIG. 4), the swing arm 72 is moved towards a first position (FIG. 4) where the actuator portion 76 moves the valve 70 to its open position (also FIG. 4) or allows the valve 70 to move to its open position (FIG. 4) to open the flow path. When the motor 64 is turning in a second direction (counterclockwise in FIG. 6) opposite the first direction, the swing arm 72 is moved to a second position (FIG. 6) where the actuator portion 76 of the swing arm 72 moves the valve 70 to its closed position (FIG. 6) or allows the valve 70 to move to its closed position to close the flow path. Preferably, the actuating portion 76 of the swing arm 72 allows the valve 70 to move to its open position when the swing arm 72 is in its first position, and actuates the valve 70 to close the valve 70 when the swing arm 72 is in its second position.

The swing arm 72 is pivotably mounted on a pivot point 78 to allow pivoting of the swing arm 72 to move the wheel-engaging portion 74 of the swing arm 72 relative to the wheel 68. The swing arm 72 engages the wheel 68 only within a limited range of rotation about the pivot point 78 to move the swing arm 72 between its first and second positions. Urging means 80 is preferably provided to urge the swing arm 72 toward the wheel 68 when the swing arm 72 is in either of its first or second positions such that the wheel 68 engages the wheel-engaging portion 74 of the swing arm 72 when the motor 64 is reversed to move the swing arm 72 to the other of its first or second positions. Most preferably, the urging means 80 comprises a torsion spring 80 mounted adjacent the swing arm 72 for urging the wheel-engaging portion 74 of the swing arm 72 toward the wheel 68.

The wheel 68 and wheel-engaging portion 74 of the swing arm 72 preferably include intermeshing teeth 82 and 84. As illustrated in FIG. 4, four teeth 84 may be provided on the wheel-engaging portion 74 of the swing arm 72.

Preferably, the valve 70 comprises a valve member 86 movable between the open and closed positions (FIGS. 4 and 6), a stem 88 extending from the valve member 86, and a spring-loaded mechanism 90 mounted on the stem 88. The spring-loaded mechanism 90 is adapted for engagement with the actuating portion 76 of the swing arm 72 to move the valve member 86 to its closed position when the swing arm 72 moves to its second position, while providing a short delay before shutting off the flow of fluid through the IV tubing 62 with the valve 70.

Most preferably, the spring-loaded mechanism 90 includes an actuating member 92 mounted on the stem 88 for axial movement along the stem 88; a spring 94 mounted on the stem 88 for biasing the actuating member 72 in the direction toward the actuating portion 76 of the swing arm 72; and a stop 96 on the stem 88 for limiting axial movement of the actuating member 92 such that the actuating member 92 does not engage the actuating portion 76 of the swing arm 72 until the swing arm 72 is moved toward its second position. The valve member 86 is free to move within a range of axial motion when the swing arm 72 is in its second position such that the valve member 86 is adapted to be biased toward its open position by the IV tubing set 62.

Many aspects of the pump 60 may be chosen from expedients known to those of skill in the art to suit the particular therapeutic purpose for which the pump is designed. In particular, the pumping mechanism which actually drives fluid though the IV tubing assembly 62 may be a syringe, linear peristaltic or rotary peristaltic pump, provided the pump has a rotary motor which is reversed on the detection of occlusion. Most preferably, however, the pumping mechanism is similar to the pumping mechanism employed in the "Model 480" infusion pump sold by Minnesota Mining and Manufacturing Company, and described in the Background of the Invention with respect to FIG. 1 and the patents and applications incorporated by reference above. Specific features of pump 60 which are the same as or similar to features of the prior infusion pump illustrated in FIG. 1 will be described with reference to FIG. 1 with the reference numerals enclosed in parenthesis.

Most preferably, the infusion pump 60 is adapted for use with a tubing set having a flexible pumping cassette (similar to cassette 40 in FIG. 1) having first and second pumping chambers (54 and 56) which are driven by pistons (46 and 48). An overpressure piston (34) is provided which is responsive to pressure in an overpressure chamber (38) of the pumping cassette (40), and is operatively linked with the valve member 86 shown in FIGS. 4–6 such that the valve member 86 is held in its closed position by the overpressure piston (34) until a predetermined cracking pressure is exerted by the overpressure chamber (38) against the overpressure piston (34).

Most desirably, the overpressure piston (34) is a spring-loaded piston (34) having biasing means (36) adapted for biasing the overpressure piston (34) against the overpressure chamber (38) of the IV tubing set 62. The overpressure piston (34) includes releasable valve-holding means (42) for holding the valve member 86 in its closed position until a predetermined cracking pressure is exerted by the overpressure chamber (38) against the overpressure piston (34) such that the valve-holding means (42) does not prevent movement of the valve member 86 between its open and closed positions once the predetermined cracking pressure has been exceeded. For example, the valve member 86 may include a pin (42) extending from the valve member 86, and the releasable valve-holding means (44) may comprise a pin-receiving slot (44) extending generally in the longitudinal direction along the piston (34). The pin-receiving slot (44) has an end adapted to engage the pin (42) to hold the valve member 86 in its closed position until the piston (34) is displaced as the overpressure chamber (38) exceeds the predetermined cracking pressure.

As illustrated in FIG. 3, a door 102 is mounted on the infusion pump 60 for holding the IV tubing set 62 in operative engagement with the pumping mechanism of the infusion pump 60. Most preferably, the door 102 covers substantially the entire frontal surface of the infusion pump 60 and includes various input and display means for controlling and displaying various operating parameters and conditions, for example, flow rate and alarm conditions.

Figure 6:
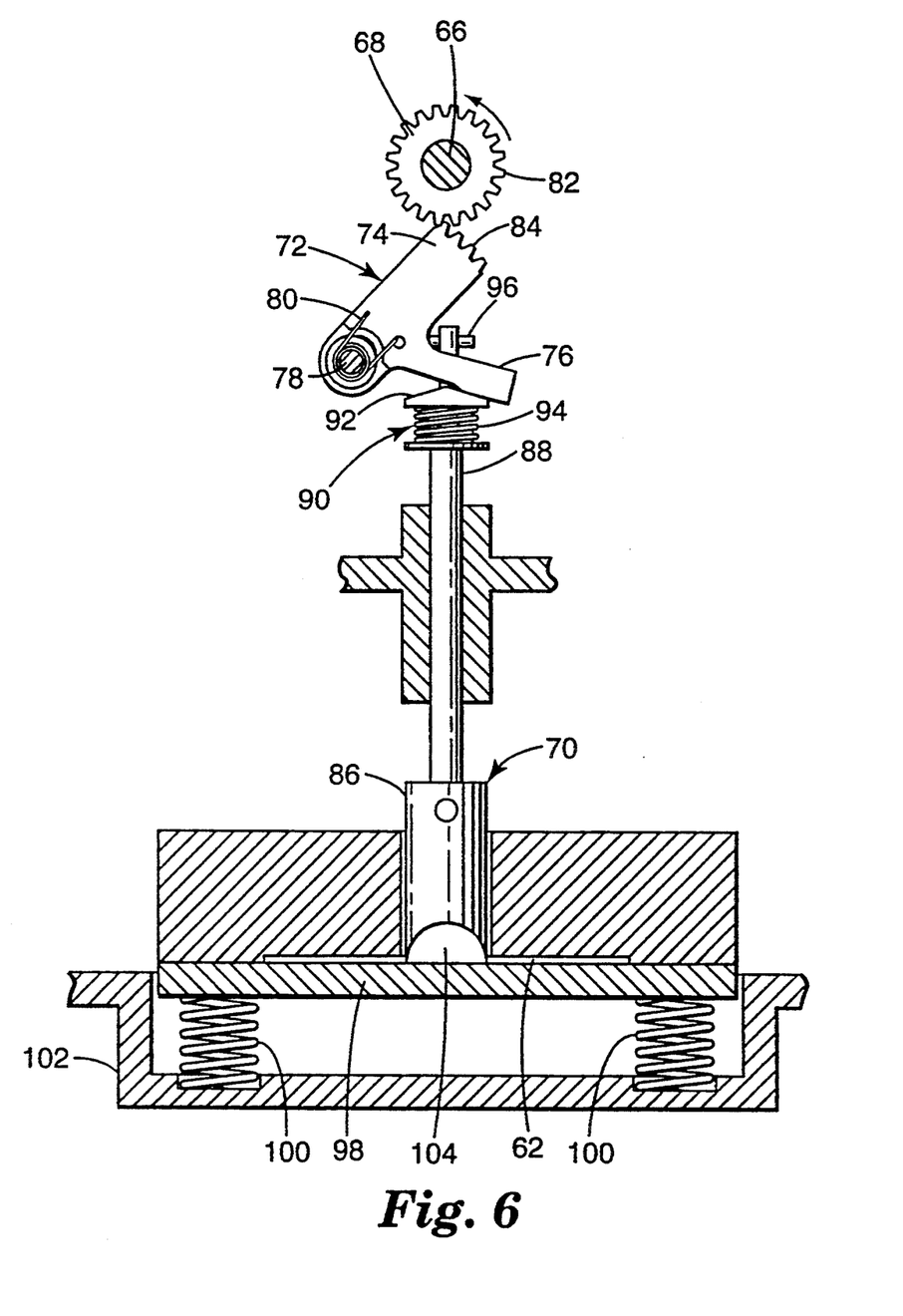
FIG. 6 is a cross sectional view similar to FIG. 4 illustrating the swing arm/valve arrangement in their closed positions in which the valve occludes the lumen of the IV tubing set.

As illustrated in FIGS. 4 and 6, the door 102 includes a floating pressure plate 98 resiliently biased by a biasing means 100 so that the pressure plate 98 is pressed against the housing of the pumping mechanism when the door 102 is closed. The biasing means 100 conveniently comprises a plurality of coil springs 100 mounting the pressure plate 98 on the door 102, and biasing the pressure plate 98 in the direction toward the pumping mechanism and valve 70. When in its closed position (FIG. 6), the valve 70 presses the IV tubing set 62 against the pressure plate 98 to close the flow path. The floating pressure plate 98 accommodates minor misalignment of the door 102 relative to the pumping mechanism, while maintaining the pumping cassette (40) in operative engagement with the pumping mechanism.

In particularly preferred embodiments, the valve member 86 will have a shape adapted to squeeze the IV tubing set 62 so as to close the fluid flow path when the valve 70 is in its closed position. This is conveniently accomplished by providing the valve member 86 with a wedge-shaped end 104. The wedge-shaped end 104 is generally flat in the direction transverse to the intended flow path. The bias of the pressure plate 98 tends to automatically align the pressure plate 98 with respect to the flat end of the valve member 86 when the door 102 is closed.

An occlusion detection means is preferably provided for detecting an occlusion in the flow path and providing a signal representing the occlusion. One example of an occlusion detection means is the overpressure piston (34), circular contact plate (55) and contact probes (57 and 58) described above with respect to FIG. 1. Most preferably, however, the occlusion detection means comprises a thin solid state electronic pressure sensor 106 mounted on the floating pressure plate 98 to sense pressure in the overpressure chamber (38) of the IV tubing set. A pump control mechanism, such as a microprocessor, acts on the signal, causing the motor 64 to be reversed in response to the signal, which causes the swing arm 72 to be moved from its first position to its second position.

Figure 5:
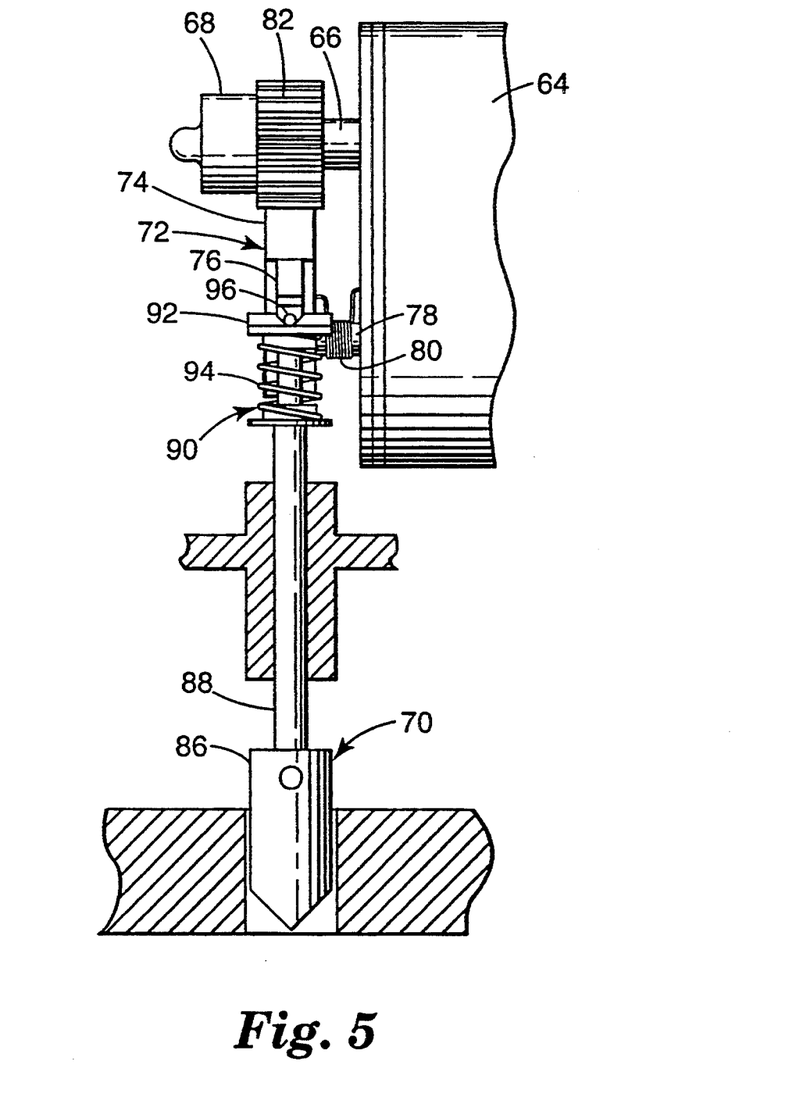
FIG. 5 is a side view of the swing arm/valve arrangement shown in FIG. 4.
Figure 7:
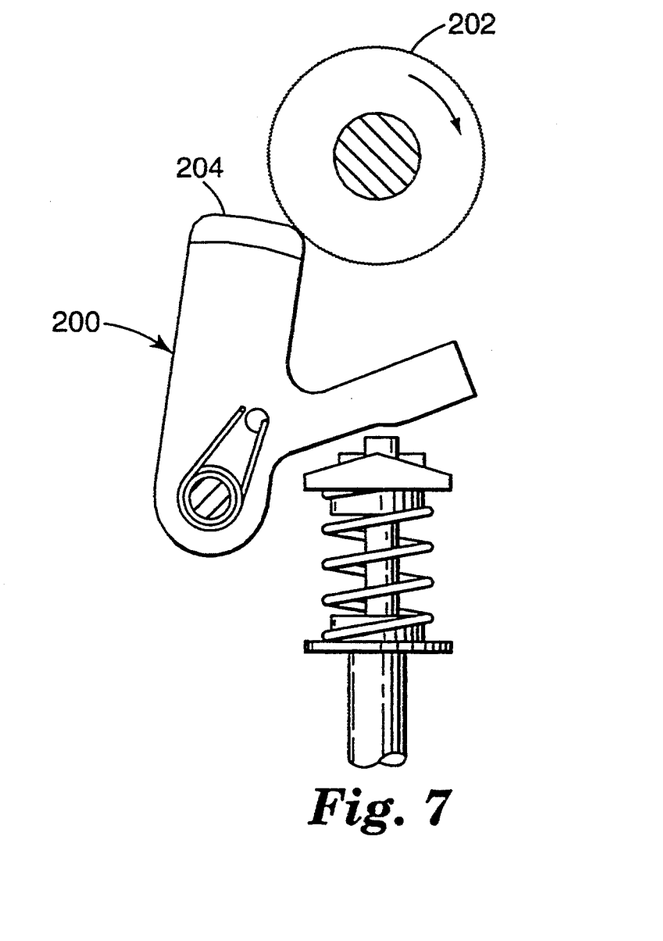
FIG. 7 is a view of a first alternative embodiment of the swing arm of the invention.

FIG. 7 illustrates an alternative embodiment of the of the swing arm and wheel, herein designated 200 and 202, respectively, similar in many respects to the swing arm 72 of FIGS. 4-6 except that the swing arm 200 and wheel 202 are both toothless. In this embodiment, at least one of the swing arm 200 and wheel 202 are provided with a surface, e.g., surface 204, having a high coefficient of friction. For example, the wheel-engaging surface 204 of the swing arm 200 may be formed by an elastomeric coating or end portion on the end of the swing arm 200. Some preferred elastomeric materials include styrene-butadiene available under the trademark "KRATON D" from Shell Chemical Co., Houston, Tex., natural rubber, and BUNA-N.

As one alternative, the swing arm may be integrally molded of a solid polymeric material, such as acetal resin available under the trademark "DELRIN" from E.I. Du Pont DeNemours & Co., Wilmington, Del., and the wheel may be provided with one of the elastomeric coatings identified above. As used herein, the term "integrally molded" means integrally molded in one continuous piece, without mechanically fastening or gluing separate pieces to form the part.

Figure 8:
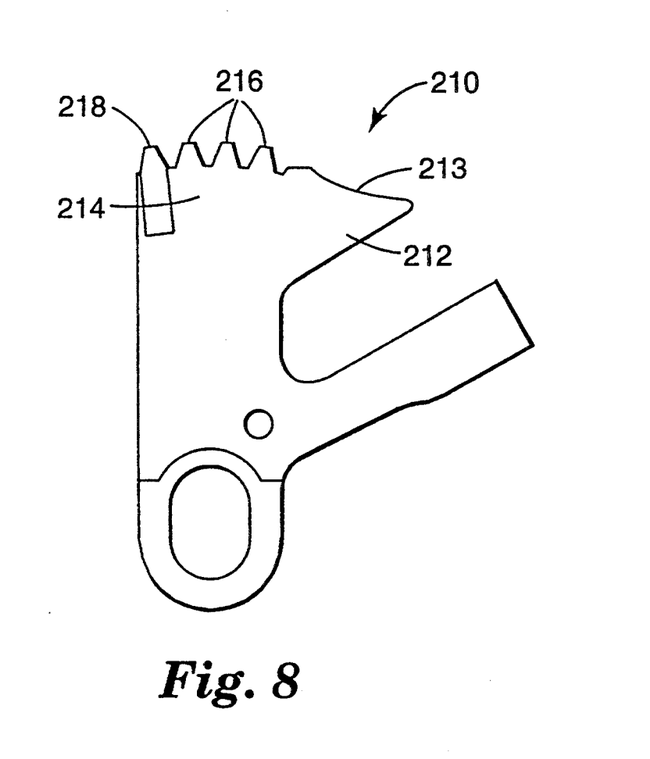
FIG. 8 is a frontal view of a second alternative embodiment of the swing arm of the invention.

FIG. 8 illustrates another alternative embodiment of the swing arm, herein designated 210 similar in many respects to the swing arm 72 of FIGS. 4-6. The swing arm 210 includes a second wheel-engaging portion 212 of the swing arm 210 adjacent one side of the first wheel-engaging portion 214 of the swing arm 210. The first wheel-engaging portion 214 includes a plurality of teeth 216 for intermeshing engagement with the teeth of the wheel (not shown but similar to wheel 68 of FIGS. 4-6), and the second wheel-engaging portion 212 has a generally concave, toothless, ramping surface 213 upon which the teeth of the wheel run without engaging the teeth of the first wheel-engaging portion 214 of the swing arm 210 when the swing arm 210 is in its first position and the motor is turning in its first direction. The arrangement is such that, when the direction of the motor is changed to its second direction, the ramping surface 213 of the swing arm 210 is moved by the wheel to bring the teeth 216 of the first wheel-engaging portion 214 of the swing arm 210 into intermeshing relationship with the teeth of the wheel. One advantage of the generally concave, toothless ramping surface 213 is that the swing arm 210 is quieter when the motor is running in the first direction.

The teeth 216 of the swing arm 210 may include an elastomeric tooth 218 adjacent the opposite side of the swing arm 210 from the second wheel-engaging portion 212 of the swing arm 210. For example, the elastomeric tooth 218 may be a rubber insert 218. The elastomeric tooth 218 may engage the teeth of the wheel during the short time interval that the motor is reversed to rotate the wheel in its second direction, and is believed to be quieter than having a metal tooth in this position. The other teeth of this embodiment may be formed of metal, or all of the teeth may be formed of elastomeric material.

Figure 9:
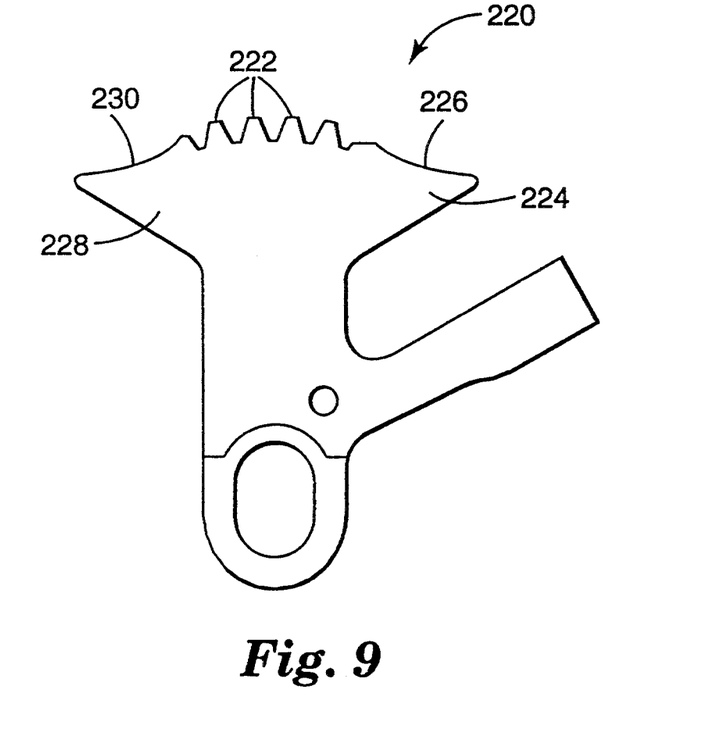
FIG. 9 is a frontal view of a third alternative embodiment of the swing arm of the invention.

FIG. 9 illustrates yet another alternative embodiment of the swing arm, herein designated 220, that is similar in many respects to the swing arm 210 of FIG. 8. The swing arm 220 has a toothed first wheel-engaging portion 222 similar to the first wheel-engaging portion 216 of FIG. 8 except that FIG. 9 does not show an elastomeric tooth, and a second wheel-engaging portion 224 having a generally concave, toothless, ramping surface 226 similar to the second wheel-engaging portion 212 of FIG. 8. In addition, the swing arm 220 has a third-wheel engaging portion 228 having a generally concave, toothless, ramping surface 230 similar in some respects to ramping surface 226. When the swing arm 220 is in its second position and the motor is running in its second direction, the teeth of the wheel (not shown but similar to the wheel 68 of FIGS. 4-6) run along the ramping surface 230 of the third wheel-engaging portion 228 of swing arm 220 without engaging the teeth of the first wheel-engaging portion 222 of the swing arm 220. In this embodiment, the swing arm 220 may be integrally molded of polymeric material to form one solid, continuous piece. A example of such a polymeric material is the acetal resin available under the trademark "DELRIN" from E.I. Du Pont DeNemours & Co., Wilmington, Del.

Figures 10, 11, 12:
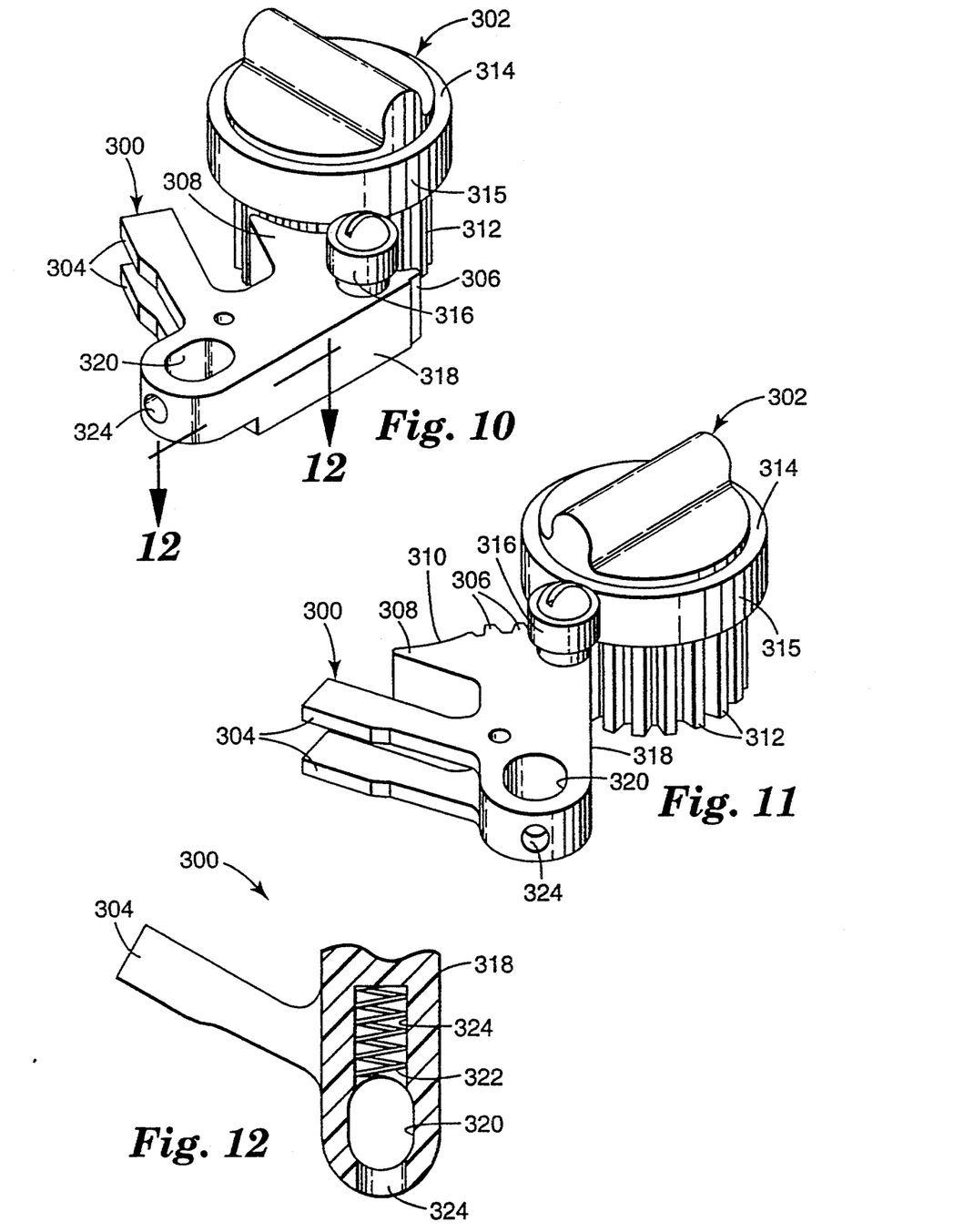
FIG. 10 is a perspective view of another preferred embodiment of the swing arm and a gear, illustrating the swing arm's position during normal operation of the infusion pump.
FIG. 11 is a perspective view similar to FIG. 10, illustrating the swing arm's position after the pump motor has been reversed.
FIG. 12 is a cross sectional view through a portion of the swing arm of FIGS. 11 and 12, illustrating details of the swing arm.

FIG. 10–12 illustrate a preferred embodiment of the swing arm and wheel of the invention, herein designated 300 and 302, respectively, similar in many respects to the swing arms 72, 210 and 220 and wheel 68 of the FIGS. 4-6, 8 and 9. Merely as a matter of illustration, FIGS. 10-13 show the swing arm 300 and wheel 302 from a different perspective than FIGS. 4-9 in which the opposite side of the swing arm and wheel are shown. In the example illustrated in FIGS. 10-13, the swing arm 300 and wheel 302 are particularly adapted for use with a valve (similar to valve 70 of FIGS. 4-6) that is biased to its open position and is movable by the swing arm 300 against the bias of the valve to its closed position.

The swing arm 300 includes an actuator portion 304 similar to actuator portion 76 of FIGS. 4-6; a toothed, first wheel-engaging portion 306 similar to the first wheel-engaging portions 74, 214, 222 of FIGS. 4-6, 8 and 9, respectively; and a second wheel-engaging portion 308 having a generally concave, toothless, ramping surface 310 similar to the second wheel-engaging portions 212 and 224 of FIGS. 8 and 9. When the motor is running in its normal pumping direction to turn the drive shaft in its first or normal operating direction (counterclockwise in FIG. 10), the swing arm 300 is in its first position (FIG. 10). In this position, the toothed, first arm-engaging portion 312 of the wheel 302 runs along the concave, ramping surface 310 of the second wheel-engaging portion 308 without the teeth of the wheel 302 engaging the teeth of the toothed, first wheel-engaging portion 306 of the swing arm 300. Also, in this position, the actuator portion 304 does not force the valve (similar to valve 70) to its closed position, so that the valve is free to move to its open position to allow flow through the lumen of the IV tubing set, assuming the overpressure chamber has exerted the "cracking" pressure on the overpressure piston (34).

The wheel 302 includes a second arm-engaging portion 314 having a toothless, cylindrical outer surface 315. The second arm-engaging portion 314 of the wheel 302 is offset axially relative to the first arm-engaging portion 312 of the wheel 302. The first and second arm-engaging portions 312 and 314 of this example form one unit that rotates as a unit. The first and second arm-engaging portions 312 and 314 of the wheel 302 may be integrally molded in one continuous piece, or may be mechanically or otherwise fastened together. Most preferably, the surface 314 of the second arm-engaging portion 314 is formed of elastomeric material, such as natural rubber or silicone rubber, and may be considered as a kind of a tire mounted on the wheel 302. The other parts of the wheel 302 may be integrally or otherwise molded of synthetic resin material, such as the acetal resin available under the trademark "DELRIN" from E.I. Du Pont DeNemours & Co., Wilmington, Del., or preferably nylon having internal lubrication.

The swing arm 300 includes a third wheel-engaging portion 316 for engaging the second arm-engaging portion 314 of the wheel 302 when the swing arm 300 is in its second position (FIG. 11) to hold the valve in its closed position. The third wheel-engaging portion 316 of the swing arm 300 preferably comprises a roller 316 that is in rolling engagement with the second arm-engaging portion 314 of the wheel 302 when the swing arm 300 is in its second position (FIG. 11) but that is disengaged from the wheel 302 as the swing arm 300 is moved toward its first position (FIG. 10).

The roller 316 holds the swing arm 300 in its second position (FIG. 11), with the teeth of the wheel 302 away from the teeth of the first wheel-engaging portion 306 of the swing arm 300, when the motor is running in its reversed direction to turn the wheel 302 in its second direction (clockwise in FIG. 11). When the direction of the motor is changed from its second direction to its first direction (i.e., its normal operating or pumping direction), the second arm-engaging portion 314 of the wheel 302 moves the roller 316 of the swing arm 300 to pivot the swing arm 300 and bring the teeth of the first wheel-engaging portion 306 of the swing arm 300 into intermeshing relationship with the teeth of the first arm-engaging portion 312 of the wheel 302.

Most preferably, a generally cylindrical axle (similar to axle 78 of FIGS. 4-6) is mounted in the infusion pump to provide a pivot axis for pivotably mounting the swing arm 300. The actuator portion 304 and first wheel-engaging portion 306 of the swing arm 300 are each generally elongate, with the longitudinal axis of the wheel-engaging arm 318 extending through the axle.

Most preferably, an "elongate" bore 320 is provided in the swing arm 300 for receiving the axle. As used herein, "elongate bore" means a bore having an elongate cross section as illustrated at 320 in FIG. 12. The elongate bore 320 is elongate in the longitudinal direction of the wheel-engaging arm 318 to permit longitudinal movement of the wheel-engaging arm 318 within a limited range of longitudinal movement. The amount of movement permitted is preferably at least as great as the depth of the teeth of the wheel 302 and/or the teeth of the first wheel-engaging portion 306 of the swing arm 300 to allow the intermeshing teeth to disengage to prevent jamming of the wheel 302 by the swing arm 300.

A suitable biasing means, such as coil compression spring 322, is provided to bias the wheel-engaging arm 318 of the swing arm 300 in the direction relative to the axle 78 toward the wheel 302. The spring 322 is adapted to maintain the teeth of the swing arm 300 and wheel 302 in intermeshing relationship when the swing arm 300 is between its first and second positions unless and until the biasing force of the spring 322 is exceeded.

A second bore 324 is provided in the swing arm 300 to receive the spring 322 and facilitate assembly of the spring 322 into the swing arm 300 before placing the swing arm 300 on the axle. The second bore 324 is not elongate in the sense used herein, but has a depth extending generally in the longitudinal direction of the wheel engaging arm 318, with the second bore 324 intersecting the elongate bore 320. The second bore 324 has a depth extending in the direction of elongation of the elongate bore 320 so that the spring 322 received in the second bore 324 applies force in the direction of elongation of elongate bore 320.

The swing arm 300 is preferably formed of aluminum.

OPERATION

When the infusion pump is first turned on the wheel 302 rotates in the first direction (counterclockwise in FIG. 10), bringing the swing arm 300 to its first position in which the ramping surface 310 is adjacent the teeth of the first arm-engaging portion 312 of the wheel 302. At this position, the valve is free to move to its open position to allow flow through the IV tubing set.

If the infusion pump is turned off or an occlusion fault condition is detected, the pump motor reverses to turn the wheel 302 in the second direction (clockwise in FIG. 11). This reversal causes the second arm-engaging portion 314 of the wheel 302 to bring the teeth of the first wheel-engaging portion 306 into intermeshing engagement with the teeth of the first arm-engaging portion 312 of the wheel, thus pivoting the swing arm 300 to its second position. The combination of the arc that the swing arm 300 pivots through and the spring-loaded mechanism 90 provides a short delay before the valve closes the fluid path to additional flow. That delay allows some pressure relief in the IV line downstream of the infusion pump. The second arm-engaging portion 314 of the wheel 302 engages the roller 316 to hold the swing arm 300 in its second position, thereby holding the valve in its closed position.

As various changes could be made in the above constructions and methods without departing from the scope of the invention, it is intended that all matter contained in the above description or shown in the accompanying drawing be interpreted as illustrative and not in a limiting sense.

We claim:

1. An infusion pump for regulating fluid flow through the flow path of an IV tubing set for intravenous administration to a patient, the infusion pump comprising:
   a pumping mechanism adapted for regulating fluid flow through the IV tubing set, the pumping mechanism comprising a reversible motor having a drive shaft with a Wheel mounted thereon;
   a valve adapted for reversibly closing the flow path through the IV tubing set, the valve having an open position, wherein the valve is adapted not to close the flow path through the IV tubing set, and a closed position, wherein the valve is adapted to close the flow path through the IV tubing set; and
   a swing arm having a wheel-engaging portion adapted for engaging the wheel and an actuator portion operatively linked with the valve such that, when the motor is turning the drive shaft in a first direction, the swing arm is moved towards a first position where the actuator portion moves the valve to its open position or allows the valve to move to its open position to open the flow path, and, when the motor is reversed to turn the drive shaft in a second direction opposite the first direction, the swing arm is moved to a second position where the actuator portion moves the valve to its closed position or allows the valve to move to its closed position to close the flow path.

2. An infusion pump according to claim 1 further comprising occlusion detection means for detecting an occlusion in the flow path and providing a signal representing the occlusion, the motor being reversed in response to a signal representing an occlusion fault being received from the occlusion detection means, the swing arm being moved from its first position to its second position when the motor is reversed; the occlusion detection means comprising a pressure sensor on the infusion pump for sensing fluid pressure in the IV tubing.

3. An infusion pump according to claim 1 wherein the swing arm is pivotably mounted on a pivot point, the wheel-engaging portion of the swing arm engaging the wheel only within a limited range of rotation about the pivot point to move the swing arm between its first and second positions, the infusion pump further comprising urging means to urge the swing arm toward the wheel when the swing arm is in either of its first or second positions such that the wheel engages the wheel-engaging portion of the swing arm when the motor is reversed to move the swing arm to the other of its first or second positions.

4. An infusion pump according to claim 3 wherein the urging means comprises a torsion spring mounted adjacent the swing arm for urging the wheel-engaging portion of the swing arm toward the wheel.

5. An infusion pump according to claim 3 wherein the wheel and wheel-engaging portion of the swing arm include intermeshing teeth.

6. An infusion pump according to claim 5 wherein the wheel-engaging portion of the swing arm constitutes a first wheel-engaging portion including the aforesaid teeth, the swing arm further having a second wheel-engaging portion comprising a generally concave, toothless, ramping surface upon which the teeth of the wheel run without engaging the teeth of the wheel-engaging portion of the swing arm when the swing arm is in its first position and the motor is turning in its first direction, the arrangement being such that, when the direction of the motor is changed to its second direction, the ramping surface of the swing arm is moved by the wheel to bring the teeth of the first wheel-engaging portion of the swing arm into intermeshing relationship with the teeth of the wheel.

7. An infusion pump according to claim 6 wherein the actuating portion of the swing arm engages the valve to close the flow path when the actuating portion is in its second position;
   the wheel comprising two arm-engaging portions including a first arm-engaging portion having the aforesaid teeth, and a second arm-engaging portion offset axially along the wheel from the first arm-engaging portion;
   the swing arm including a third wheel-engaging portion for engaging the second arm-engaging portion of the wheel when the swing arm is in its second position to hold the swing arm in its second position when the motor is turning in its second direction, without the teeth of the first wheel-engaging portion of the swing arm engaging the teeth of the first arm-engaging portion of the wheel, thereby holding the valve in its closed position; the arrangement being such that, when the direction of the motor is changed from its second direction to its first direction, the second arm-engaging portion of the wheel moves the third wheel-engaging portion of the swing arm to pivot the swing arm and bring the teeth of the first wheel-engaging portion of the swing arm into intermeshing relationship with the teeth of the first arm-engaging portion of the wheel.

8. An infusion pump according to claim 7 wherein the third wheel-engaging portion of the swing arm comprises a roller that is in rolling engagement with the second arm-engaging portion of the wheel when the swing arm is in its second position but that is disengaged from the wheel as the swing arm is moved toward its first position.

9. An infusion pump according to claim 6 wherein the second wheel-engaging portion of the swing arm is adjacent one side of the first wheel-engaging portion of the swing arm, the teeth of the swing arm include at least one elastomeric tooth adjacent the opposite side of the swing arm from the second wheel-engaging portion of the swing arm.

10. An infusion pump according to claim 3 further comprising a axle mounted in the pump for pivotably mounting the swing arm, the swing arm being elongate and having:
    an elongate bore having an elongate cross section for receiving the axle to permit longitudinal movement of the swing arm within a limited range of longitudinal movement; and
    a biasing means for biasing the swing arm in the longitudinal direction relative to the axle generally toward the wheel.

11. An infusion pump according to claim 1 wherein the actuating portion of the swing arm allows the valve move to its open position when the swing arm is in its first position and actuates the valve to close the valve when the swing arm is in its second position;
    the valve comprising a valve member movable between the open and closed positions, a stem extending from the valve member, and a spring-loaded mechanism mounted on the stem for engagement with the actuating portion of the swing arm to move the valve member to its closed position when the swing arm moves to its second position while providing a short delay before shutting off the flow of fluid through the IV tubing with the valve;

the spring-loaded mechanism including an actuating member mounted on the stem for axial movement along the stem, a spring mounted on the stem for biasing the actuating member in the direction toward the actuating portion of the swing arm, and a stop on the stem for limiting axial movement of the actuating member such that the actuating member does not engage the actuating portion of the swing arm until the swing arm is moved toward its second position.

12. An infusion pump according to claim 11 wherein the valve member is free to move within a range of axial motion when the swing arm is in its second position such that the valve member is adapted to be biased toward its open position by the IV tubing set.

13. An infusion pump according to claim 11 of the type adapted to receive an IV tubing set having a pumping cassette having one or more pumping chambers for pumping fluid through the IV tubing and an overpressure chamber responsive to pressure in the IV tubing; the infusion pump further comprising an overpressure piston responsive to pressure in the overpressure chamber and operatively linked with the valve member such that the valve member is held in its closed position by the overpressure piston until a predetermined cracking pressure is exerted by the overpressure chamber against the overpressure piston;

the overpressure piston comprising a spring-loaded piston having biasing means adapted for biasing the piston against the overpressure chamber of the IV tubing set;

the piston including releasable valve-holding means for holding the valve member in its closed position until a predetermined cracking pressure is exerted by the overpressure chamber against the overpressure piston such that the valve-holding means does not prevent movement of the valve member between its open and closed positions once the predetermined cracking pressure has been exceeded; and the valve member including a pin extending from the valve member, the releasable valve-holding means comprising a pin-receiving slot extending generally in the longitudinal direction along the piston, the pin-receiving slot having an end adapted to engage the pin to hold the valve member in its closed position until the piston is displaced as the overpressure chamber exceeds the predetermined cracking pressure.

14. An infusion pump according to claim 1 further comprising a door mounted on the infusion pump and a floating pressure plate mounted in the door of the infusion pump for holding the IV tubing set in operative position relative to the pumping mechanism when the door is closed, the pressure plate being biased toward the pumping mechanism and the valve to hold the IV tubing set between the pressure plate and the pumping mechanism;

the valve when in its closed position pressing the IV tubing set against the pressure plate to close the fluid path, the valve including a valve member having a valve member adapted to squeeze the IV tubing set to close the fluid flow path when the valve is in its closed position, the valve member being generally flat in the direction transverse to the intended flow path, the pressure plate being movably mounted on the door and biased in the direction that is toward the valve member when the door is closed such that the bias of the pressure plate tends to automatically align the pressure plate with respect to the valve member when the door is closed.

15. An infusion therapy system for regulating fluid flow for intravenous administration to a patient, the system comprising an IV tubing set having a flow path for fluid, and an infusion pump for regulating fluid flow through the IV tubing set, the infusion pump comprising:

a valve for reversibly closing the flow path through the IV tubing set, the valve having an open position, wherein the valve does not close the flow path through the IV tubing set, and a closed position, wherein the valve closes the flow path through the IV tubing set;

a pumping mechanism for regulating fluid flow through the IV tubing set, the pumping mechanism comprising a reversible motor having a drive shaft with a wheel mounted thereon; and a swing arm having a wheel-engaging portion adapted to engage the wheel and an actuator portion operatively linked with the valve such that, when the motor is turning in a first direction, the swing arm is moved towards a first position where the actuator portion moves the valve in its open position or allows the valve to move to its open position to open the flow path through the IV tubing set, and, when the motor is turning in a second direction opposite the first direction, the swing arm is moved to a second position where the actuator portion moves the valve to its closed position or allows the valve to move to its closed position to close the flow path through the IV tubing set.

16. An infusion therapy system according to claim 15 further comprising occlusion detection means for detecting an occlusion in the flow path and providing a signal representing the occlusion, the motor being reversed in response to a signal representing an occlusion fault being received from the occlusion detection means, the swing arm being moved from its first position to its second position when the motor is reversed; the occlusion detection means comprising a pressure sensor on the infusion pump for sensing fluid pressure in the IV tubing.

17. An infusion therapy system according to claim 15 wherein the swing arm is pivotably mounted on a pivot point, the swing arm engaging the wheel only within a limited range of rotation about the pivot point to move the swing arm between its first and second positions, the infusion pump further comprising urging means to urge the swing arm toward the wheel when the swing arm is in either of its first or second positions such that the wheel engages the wheel-engaging portion of the swing arm when the motor is reversed to move the swing arm to the other of its first or second positions.

18. An infusion therapy system according to claim 17 wherein the urging means comprises a torsion spring mounted adjacent the swing arm for urging the wheel-engaging portion of the swing arm toward the wheel.

19. An infusion therapy system according to claim 17 wherein the wheel and wheel-engaging portion of the swing arm include intermeshing teeth.

20. An infusion therapy system according to claim 19 wherein the wheel-engaging portion of the swing arm constitutes a first wheel-engaging portion including the aforesaid teeth, the swing arm further having a second wheel-engaging portion comprising a generally concave, toothless, ramping surface upon which the teeth of the wheel run without engaging the teeth of the wheel-engaging portion of the swing arm when the swing arm is in its first position and the motor is turning in its first direction, the arrangement being such that, when the direction of the motor is changed to its second direction, the ramping surface of the swing arm is moved by the wheel to bring the teeth of the first wheel-engaging portion of the swing arm into intermeshing relationship with the teeth of the wheel.

21. An infusion therapy system according to claim 20 wherein the actuating portion of the swing arm engages the valve to close the flow path when the actuating portion is in its second position;
  the wheel comprising two arm-engaging portions including a first arm-engaging portion having the aforesaid teeth, and a second arm-engaging portion offset axially along the wheel from the first arm-engaging portion;
  the swing arm including a third wheel-engaging portion for engaging the second arm-engaging portion of the wheel when the swing arm is in its second position to hold the swing arm in its second position when the motor is turning in its second direction, without the teeth of the first wheel-engaging portion of the swing arm engaging the teeth of the first arm-engaging portion of the wheel, thereby holding the valve in its closed position; the arrangement being such that, when the direction of the motor is changed from its second direction to its first direction, the second arm-engaging portion of the wheel moves the third wheel-engaging portion of the swing arm to pivot the swing arm and bring the teeth of the first wheel-engaging portion of the swing arm into intermeshing relationship with the teeth of the first arm-engaging portion of the wheel;
  the third wheel-engaging portion of the swing arm comprising a roller that is in rolling engagement with the second arm-engaging portion of the wheel when the swing arm is in its second position but that is disengaged from the wheel as the swing arm is moved toward its first position.

22. An infusion therapy system according to claim 20 wherein the second wheel-engaging portion of the swing arm is adjacent one side of the first wheel-engaging portion of the swing arm, the teeth of the swing arm include at least one elastomeric tooth adjacent the opposite side of the swing arm from the second wheel-engaging portion of the swing arm.

23. An infusion therapy system according to claim 17 further comprising a axle mounted in the pump for pivotably mounting the swing arm, the swing arm being elongate and having:
  an elongate bore having an elongate cross section for receiving the axle to permit longitudinal movement of the swing arm within a limited range of longitudinal movement; and
  a biasing means for biasing the swing arm in the longitudinal direction relative to the axle generally toward the wheel.

24. An infusion therapy system according to claim 15 wherein the actuating portion of the swing arm allows the valve move to its open position when the swing arm is in its first position and actuates the valve to close the valve when the swing arm is in its second position;
  the valve comprising a valve member movable between the open and closed positions, a stem extending from the valve member, and a spring-loaded mechanism mounted on the stem for engagement with the actuating portion of the swing arm to move the valve member to its closed position when the swing arm moves to its second position while providing a short delay before shutting off the flow of fluid through the IV tubing with the valve;
  the spring-loaded mechanism including an actuating member mounted on the stem for axial movement along the stem, a spring mounted on the stem for biasing the actuating member in the direction toward the actuating portion of the swing arm, and a stop on the stem for limiting axial movement of the actuating member such that the actuating member does not engage the actuating portion of the swing arm until the swing arm is moved toward its second position.

25. An infusion therapy system according to claim 24 wherein the valve member is free to move within a range of axial motion when the swing arm is in its second position such that the valve member is adapted to be biased toward its open position by the IV tubing set.

26. An infusion therapy system according to claim 25 wherein the IV tubing set further includes a pumping cassette adapted to be received in the pumping mechanism of the infusion pump, the pumping cassette having one or more pumping chambers for pumping fluid through the IV tubing and an overpressure chamber responsive to pressure in the IV tubing; and the infusion pump further comprises an overpressure piston responsive to pressure in the overpressure chamber and operatively linked with the valve member such that the valve member is held in its closed position by the overpressure piston until a predetermined cracking pressure is exerted by the overpressure chamber against the overpressure piston.

27. An infusion therapy system according to claim 26 wherein the overpressure piston comprises a spring-loaded piston having biasing means adapted for biasing the piston against the overpressure chamber of the IV tubing set;
  the piston including releasable valve-holding means for holding the valve member in its closed position until a predetermined cracking pressure is exerted by the overpressure chamber against the overpressure piston such that the valve-holding means does not prevent movement of the valve member between its open and closed positions once the predetermined cracking pressure has been exceeded; and
  the valve member including a pin extending from the valve member, the releasable valve-holding means comprising a pin-receiving slot extending generally in the longitudinal direction along the piston, the pin-receiving slot having an end adapted to engage the pin to hold the valve member in its closed position until the piston is displaced as the overpressure chamber exceeds the predetermined cracking pressure.

28. An infusion therapy system according to claim 15 further comprising a door mounted on the infusion pump and a floating pressure plate mounted in the door of the infusion pump for holding the IV tubing set in operative position relative to the pumping mechanism when the door is closed, the pressure plate being biased toward the pumping mechanism and the valve to hold the IV tubing set between the pressure plate and the pumping mechanism;

the valve when in its closed position pressing the IV tubing set against the pressure plate to close the fluid path, the valve including a valve member having a valve member adapted to squeeze the IV tubing set to close the fluid flow path when the valve is in its closed position, the valve member being generally flat in the direction transverse to the intended flow path, the pressure plate being movably mounted on the door and biased in the direction that is toward the valve member when the door is closed such that the bias of the pressure plate tends to automatically align the pressure plate with respect to the valve member when the door is closed.

29. For use with an infusion pump of the type having a motor-driven pumping mechanism adapted to regulate the flow of IV fluid through IV tubing for intravenous administration to a patient, the infusion pump including a valve for reversibly closing the fluid path, and a swing arm operatively linked to a wheel driven by the pump-driving motor; a method of closing the fluid path through IV tubing in response to a fault condition, such as an occlusion in IV tubing, in a manner designed to avoid supplying a bolus of IV fluid to the patient when the fluid path is closed; the method comprising the steps of:

pumping IV fluid in the downstream direction toward the patient through IV tubing with the pumping mechanism;

reversing the direction of the pump-driving motor when turning off the pump or detecting a fault condition such that the direction of rotation of the wheel is reversed and fluid is pumped in the upstream direction away from the patient;

pivoting the swing arm from a first position, in which the valve is allowed to be in an open position allowing fluid flow through the IV tubing, to a second position, in which the valve is moved to a closed position closing the IV tubing to fluid flow, in response to the direction of rotation of the wheel being reversed; and moving the valve to its closed position from its open position by actuating the valve with the swing arm in response to the swing arm being pivoted from its first position to its second position.

30. A method according to claim 29 further comprising the steps of:

turning on the pumping mechanism of the infusion pump; and opening the valve by moving the swing arm from its second position to its first position by the wheel when the pump-driving motor is turned on, thereby allowing pump-regulated fluid flow through the IV tubing.

31. A method according to claim 30 further comprising the step of urging a wheel-engaging portion of the swing arm toward the wheel when the swing arm is in either of its first and second positions such that the wheel-engaging portion of the swing arm engages the wheel when the motor is reversed to move the swing arm to the other of its first and second positions.

32. A method according to claim 31 further comprising the step of detecting an occlusion fault condition wherein the IV flow path is occluded, the step of reversing the direction of the pump-driving motor comprising reversing the direction of the pump-driving motor in response to detection of an occlusion fault condition.

33. A method according to claim 31 wherein the wheel and the wheel-engaging portion of the swing arm are of the type having intermeshing teeth, the step of pivoting the swing arm including engaging the teeth of the wheel-engaging portion of the swing arm with the teeth of the wheel to pivot the swing arm from its first to its second position.

34. A method according to claim 32 wherein the step of moving the valve to its closed position includes the step of providing a short delay before shutting off the flow of fluid through the IV tubing with the valve when the swing arm moves to its second position.

* * * * *